United States Patent [19] [11] 4,277,477
Hagen et al. [45] Jul. 7, 1981

[54] METHOD OF USING 1,2-BENZISOTHIAZOLES

[75] Inventors: Helmut Hagen, Frankenthal; Rolf-Dieter Kohler, Mannheim; Juergen Markert, Ludwigshafen, all of Fed. Rep. of Germany

[73] Assignee: BASF Aktiengesellschaft, Fed. Rep. of Germany

[21] Appl. No.: 81,059

[22] Filed: Oct. 2, 1979

Related U.S. Application Data

[62] Division of Ser. No. 926,446, Jul. 26, 1978, abandoned.

[30] Foreign Application Priority Data

Aug. 3, 1977 [DE] Fed. Rep. of Germany ....... 2734866

[51] Int. Cl.³ .......................................... C07D 275/04
[52] U.S. Cl. ................................... 424/251; 424/269; 424/270; 548/207

[58] Field of Search ................ 548/207, 212; 424/251, 424/269, 270, 275

[56] References Cited

U.S. PATENT DOCUMENTS

| 3,682,941 | 8/1972 | Becke et al. | 260/304 |
| 3,707,364 | 12/1972 | Becke | 71/90 |
| 4,140,692 | 2/1979 | Fleig et al. | 548/207 |
| 4,178,451 | 12/1979 | Wade et al. | 424/270 |

FOREIGN PATENT DOCUMENTS 2503699 8/1976 Fed. Rep. of Germany .

Primary Examiner—Nicholas S. Rizzo
Attorney, Agent, or Firm—Keil & Witherspoon

[57] ABSTRACT

Novel 1,2-benzisothiazoles and a process for the manufacture of 1,2-benzisothiazoles by reacting o-haloaryl ketones with ammonia and elementary sulfur. The compounds are starting materials for the manufacture of dyes, crop protection agents and drugs.

1 Claim, No Drawings

METHOD OF USING 1,2-BENZISOTHIAZOLES

This is a division of co-pending application Ser. No. 926,446, filed July 26, 1978, now abandoned.

The present invention relates to novel 1,2-benzisothiazoles and to a process for the manufacture of a 1,2-benzisothiazole by reacting an o-haloaryl ketone with ammonia and elementary sulfur.

Angewandte Chemie, 36 (1923), 159 and Berichte der deutschen Chemischen Gesellschaft, 58 (1925), 2,095 disclose that thionaphthene-2,3-dione may be reacted with ammonia and hydrogen peroxide to give 3-carbamyl-1,2-benzisothiazole and that 1,2-benzisothiazole may be obtained from the latter by hydrolysis and decarboxylation. Berichte, 56 (1923), 1,630 and Liebigs Annalen der Chemie, 454 (1927), 264 describe the reaction of 2-formyl-4-nitrophenylsulfenyl bromide with ammonia to give 5-nitro-1,2-benzisothiazole. Benzisothiazoles can also be synthesized by cyclizing o-mercapto-phenyl-carbonyl compounds in the presence of polyphosphoric acid (Annali di Chimica, 53 (1963), No. 5, 577–587). German Laid-Open Application DOS No. 1,670,196 discloses the reaction of dihalomethylaryl compounds with ammonia and sulfur to give benzisothiazoles. All these processes are unsatisfactory in respect to ease of access to the starting materials, economy, and simplicity of operation coupled with a good yield of end product.

German Laid-Open Application DOS No. 2,503,699 relates to a process for the manufacture of a 1,2-benzisothiazole of the formula

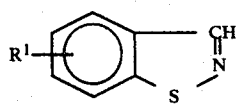

where $R^1$ is hydrogen, an aliphatic or cycloaliphatic radical, an aromatic radical which may or may not be fused, halogen, alkoxy or nitro or

where the radicals $R^2$ may be identical or different and each is hydrogen or an aliphatic, cycloaliphatic, araliphatic or aromatic radical, wherein an o-haloaryl aldehyde of the formula

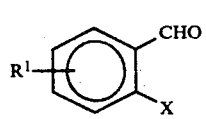

where X is halogen and $R^1$ has the above meanings, is reacted with ammonia and elementary sulfur.

We have found that a 1,2-benzisothiazole of the formula

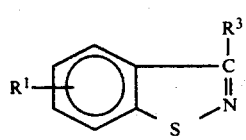

where $R^1$ is hydrogen, an aliphatic or cycloaliphatic radical, an aromatic radical which may or may not be fused, halogen, alkoxy, nitro or

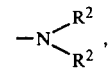

where the radicals $R^2$ may be identical or different and each is hydrogen or an aliphatic, cycloaliphatic, araliphatic or aromatic radical, and $R^3$ is an aromatic or heterocyclic radical, may be obtained in an advantageous manner by reacting an o-haloaryl ketone of the formula

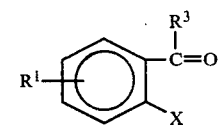

where $R^1$ and $R^3$ have the above meanings and X is halogen, with ammonia and elementary sulfur.

Further, we have found the novel 1,2-benzisothiazoles of the formula

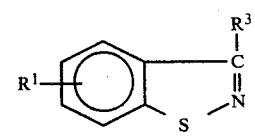

where $R^1$ is hydrogen, an aliphatic or cycloaliphatic radical, an aromatic radical which may or may not be fused, halogen, alkoxy, nitro or

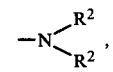

where the radicals $R^2$ may be identical or different and each is hydrogen or an aliphatic, cycloaliphatic, araliphatic or aromatic radical, and $R^3$ is a substituted mononuclear or substituted or unsubstituted polynuclear aromatic radical or is a heterocyclic radical.

By way of example, the reaction of 2-chloro-5-nitrobenzophenone with ammonia and sulfur may be represented by the following equation:

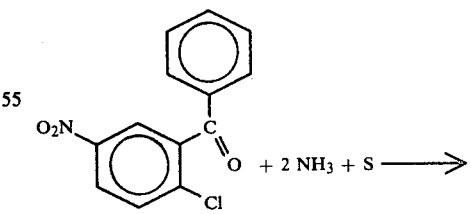

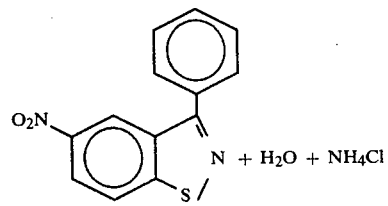

In comparison with the first-mentioned conventional process, the process of the invention uses more easily accessible starting materials and, surprisingly, gives 1,2-benzisothiazoles in a simple and economical manner, and in better yield and greater purity. Compared to German Laid-Open Application DOS No. 2,503,699, the ketones II can also be reacted, to give 1,2-benzisothiazoles, substituted by an aromatic or heterocyclic radical in the 3-position, which have not previously been described. These advantageous results are surprising in view of the prior art.

Preferred starting materials II and, accordingly, preferred 1,2-benzisothiazoles I are those where $R^1$ is alkyl of 1 to 6 carbon atoms which may or may not be substituted by a carboximido group or is cycloalkyl of 5 to 12 carbon atoms or is phenyl or naphthyl, either of which may be fused, or is a fused naphthoquinon-1,4-ylene radical, or is hydrogen, bromine or particularly chlorine, alkoxy of 1 to 4 carbon atoms, nitro or

where the radicals $R^2$ may be identical or different and each is hydrogen, alkyl of 1 to 6 carbon atoms, alkenyl of 3 to 6 carbon atoms, cycloalkyl of 5 to 8 carbon atoms, aralkyl of 7 to 12 carbon atoms or phenyl, $R^3$ is phenyl or naphthyl which are unsubstituted or substituted by one or more, preferably one or two, alkyl radicals, preferably of 1 to 4 carbon atoms, alkoxy groups, preferably of 1 to 4 carbon atoms, chlorine atoms, bromine atoms or dialkylamino groups, preferably where each alkyl is of 1 to 4 carbon atoms, or is a 5-membered or 6-membered heterocyclic ring which may contain two nitrogen atoms or one nitrogen atom, one oxygen atom and/or one sulfur atom. The above radicals may in addition be substituted by groups which are inert under the reaction conditions, eg. alkyl or alkoxy, each of 1 to 4 carbon atoms, nitro or carboxamido. Instead of the starting materials II, compounds which form these starting materials under the reaction conditions may also be used, eg. the corresponding aldehyde-acetals, eg. o-chlorobenzophenone dimethylacetal. The starting material II, ammonia and elementary sulfur may be used in about stoichiometric amounts, but it is preferred to use a ratio of from 2 to 10 moles of ammonia and/or of from 0.9 to 1.1 gram atoms of sulfur per mole of starting material II.

Examples of suitable starting materials II are 5-nitro, 4-dimethylamino-, 4-diethylamino-, 4-diallylamino-, 4-di-(2'-methylallyl)-amino-, 4-(N-methyl-N-2-carboxamidoethylamino)-, 6-methyl-, 3-ethyl-, 5-hexyl-, 6-isobutyl-, 5-propyl-, 4-tert.-butyl-, 4-cyclohexyl-, 4-cyclopentyl-, 5-phenyl-, 4-phenyl-, 4-nitrophenyl-, 4-p-toluyl-, 4-p-ethoxyphenyl-, 3-di-(2'-ethoxyethyl)-amino-, 4-naphthyl-, 4-bromo, 6-methoxy-, 6-dicyclohexylamino-, 4-dibenzylamino-, 4-diphenylamino- and 4-p-xylyl-2-chlorobenzophenone; 2-chlorobenzophenone and 2-bromobenzophenone; 1-chloro-2-benzoyl-, 2-chloro-3-benzoyl- and 2-chloro-1-benzoylnaphthalene; 1-chloro-2-benzoyl-, 2-chloro-3-benzoyl- and 2-chloro-1-benzoyl-anthraquinone; 1-chloro-2-benzoyl-, 2-chloro-3-benzoyl- and 2-chloro-1-benzoyl-anthracene; 1-chloro-2-benzoyl-, 2-chloro-3-benzoyl- and 2-chloro-1-benzoyl-phenanthrene; correspondingly substituted bromoaryl ketones; benzophenones in which both phenyl nuclei are similarly substituted with the above substituents; similar aroylbenzenes in which the aroyl radical is substituted by chlorine or bromine and the benzene nucleus carries, in the o-, m- and/or p-position, one or two methyl, ethyl, propyl, isopropyl, butyl, isobutyl, sec.-butyl, tert.-butyl, chloro, bromo, ethoxy, methoxy, propoxy, isopropoxy, butoxy, dimethylamino, diethylamino, dipropylamino, or diisopropylamino groups; aroylnaphthalenes, aroylthiophenes, aroyltetrahydrofurans, aroylpyrans and corresponding aroyl compounds of imidazole, 1-methylimidazole, 1-propylimidazole, 2-methylpyridine, 3-methylpyridine, 4-methylpyridine, 2,4-dimethylpyridine, 2,6-dimethylpyridine, 2,4,6-trimethylpyridine, pyridine, pyrrolidine, pyrrole, imidazolidine, piperidine, morpholine, pyridazine, pyrimidine, pyrazine and piperazine, in each of which the aroyl nucleus is substituted by the above substituents.

The reaction is, as a rule, carried out at from 20° to 250° C., advantageously from 20° to 200° C., preferably from 40° to 180° C., and especially from 40° to 120° C., under atmospheric or superatmospheric pressure, continuously or batchwise. The reaction pressure is in general determined by the total vapor pressure of the components at the reaction temperature. Organic solvents which are inert under the reaction conditions may or may not be used, examples of such solvents being aromatic hydrocarbons, eg. toluene, ethylbenzene, o-, m- and p-xylene and isopropylbenzene; alkanols and cycloalkanols, eg. ethanol, n-butanol, isobutanol, methylglycol, cyclohexanol, propanol, methanol and 2-ethylhexanol; ethers, eg. ethyl propyl ether, diisobutyl ether, methyl tert.-butyl ether, n-butyl ethyl ether, di-n-butyl ether, dioxane, diisoamyl ether, diisopropyl ether, anisole, phenetole, cyclohexyl methyl ether, diethyl ether, tetrahydrofuran and thioanisole, and mixtures of the above. The solvent is advantageously used in an amount of from 200 to 10,000 percent by weight, preferably from 300 to 1,000 percent by weight, based on starting material II.

The reaction may be carried out as follows: the starting material II, elementary sulfur and ammonia are reacted, in the presence or absence of a solvent, for from 3 to 10 hours at the above temperature in a pressure reactor. The 1,2-benzisothiazole I is obtained from the reaction mixture by conventional methods for example by fractional distillation and filtration, with or without subsequent recrystallization from a suitable solvent, eg. light naphtha. It is also possible to remove excess ammonia and solvent, then pour the reaction mixture into water, extract the resulting mixture with a suitable solvent, eg. methylene chloride or benzene and work up the extract in the above manner.

The compounds obtainable by the process of the invention are valuable starting materials for the manufacture of dyes, crop protection agents and drugs.

For the above uses, it is advantageous to employ the 1,2-benzisothiazoles in which $R^1$ and $R^3$ have the preferred meanings. For example, a 1,2-benzisothiazole of the formula

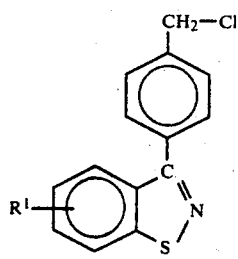

where $R^1$ has the above meanings can be reacted with a diamine of the general formula $$H_2N—Y—NH_2 \qquad III$$

where Y is a bridge member of the formula

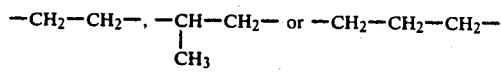

and elementary sulfur, advantageously in an inert, organic solvent, to give a compound of the formula

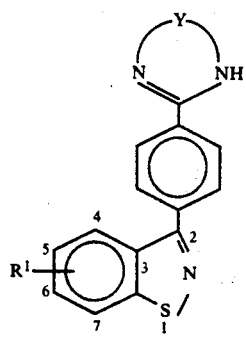

where $R^1$ has the above meanings and is, in particular, hydrogen, alkyl of 1 to 4 carbon atoms, alkoxy of 1 to 3 carbon atoms, halogen or nitro and Y has the stated meanings, and the resulting compound IV may or may not be converted into a physiologically acceptable addition salt with an acid. Amongst the given meanings, $R^1$ is preferably hydrogen, halogen, especially chlorine or bromine, nitro or alkyl or alkoxy, each of 1 to 4 carbon atoms, and Y is preferably 1-methyl-1,2-ethylene or 1,3-trimethylene. Particularly preferred meanings are $R^1$=hydrogen and Y=1-methyl-1,2-ethylene and 1,3-trimethylene.

The above reaction to give the compounds IV is advantageously carried out at from 40° to 150° C., preferably at from 70° to 120° C.

Advantageous solvents to use for the reaction to give the compounds IV are aromatic hydrocarbons, especially benzene hydrocarbons, eg. benzene or toluene, lower alcohols, eg. methanol, ethanol, propanol, isopropanol, butanol or isobutanol, saturated cyclic or aliphatic ethers, eg. dibutyl ether or dioxane, glycol ethers, especially glycol monoalkyl ethers, eg. glycol monomethyl ether or glycol monoethyl ether, and mixtures of the said solvents.

Amongst these solvents, the benzene hydrocarbons, advantageously benzene and toluene, and the glycol monoalkyl ethers, especially glycol monoethyl ether, are preferred.

The diamine of the formula III is used in stoichiometric amount or in excess, viz. up to 3 times the stoichiometric amount, based on the compound of the formula I or Ib.

The elementary sulfur is used in stoichiometric amount or in excess, viz. up to a 1.2-fold excess over the stoichiometric amount, based on compound Ib. Preferably, the stoichiometric amount of elementary sulfur is used.

By way of example, the reaction of 3-(4-chloromethylphenyl)-1,2-benzisothiazole with ethylenediamine and sulfur may be represented by the following equation:

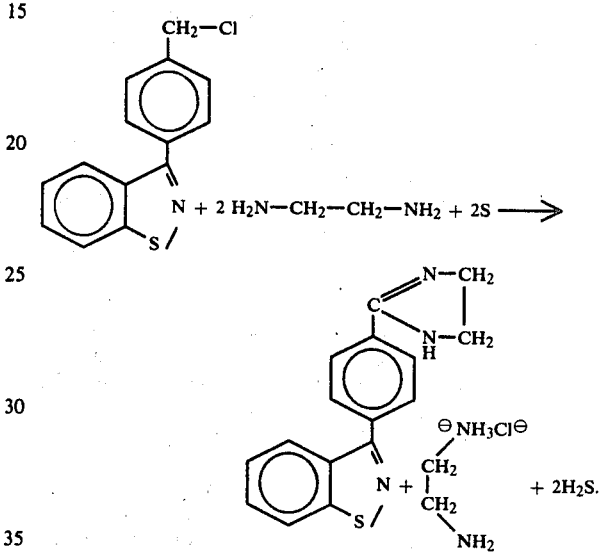

The starting compound of the formula Ib may be obtained, for example, by side-chain chlorination of a 3-(4-methylphenyl)-1,2-benzisothiazole I with chlorine at about 170° C. under UV irradiation.

The compound of the general formula IV may or may not be converted, in the conventional manner, to an addition salt with a physiologically acceptable acid. Examples of suitable conventional physiologically acceptable organic or inorganic acids are hydrochloric acid, hydrobromic acid, phosphoric acid and sulfuric acid amongst inorganic acids and oxalic acid, maleic acid, fumaric acid, lactic acid, tartaric acid, malic acid, citric acid, salicylic acid, adipic acid and benzoic acid, amongst organic acids; examples of acids may also be found in Fortschritte der Arzneimittelforschung, volume 10, pages 224–225, Birkhäuser Verlag, Basel and Stuttgart, 1966.

Examples of advantageous compounds of the formula IV are 3-[4-(imidazolin-2-yl)-phenyl]-1,2-benzisothiazole, 3-[4-(methylimidazolin-2-yl)-phenyl]-1,2-benzisothiazole, 3-[4-(tetrahydropyrimidin-2-yl)-phenyl]-1,2-benzisothiazole, 5-chloro-3-[4-(imidazolin-2-yl)-phenyl]-1,2benzisothiazole, 5-chloro-3-[4-(methylimidazolin-2-yl)-phenyl]-1,2-benzisothiazole, 4-methoxy-3-[4-(methylimidazolin-2-yl)-phenyl]-1,2-benzisothiazole, 5-nitro-3-[4-(imidazol-2-yl)-phenyl]-1,2-benzisothiazole, 5-nitro-3-[4-(tetrahydropyrimidin-2-yl)-phenyl]-1,2-benzisothiazole and 5-bromo-6-chloro-3-[4-(imidazolin-2-yl)-phenyl]-1,2-benzisothiazole.

The above 3-[4-(1,3-diazacycloalken-2-yl)-phenyl]-1,2-benzisothiazoles IV and their physiologically acceptable addition salts with acids exhibit valuable pharmacological properties. They may be used to prepare pharmaceutical formulations which contain a compound of the formula IV as the active ingredient, together with conventional pharmaceutical carriers and excipients. Particularly suitable compounds are 3-[4-(tetrahydropyrimidin-2-yl)-phenyl]-1,2-benzisothiazole and 3-[4-(methylimidazolin-2-yl)-phenyl]-1,2-benzisothiazole and their physiologically acceptable addition salts with acids. The compounds IV and their physiologically acceptable addition salts with acids are distinguished by powerful antiarrhythmic action and are in particular suitable for the pharmacotherapy of cardiac arrhythmias. The anti-arrhythmic activity of the compounds is determined by orally administering these to rats (Sprague Dawley, weight: 180–240 g) 45 minutes before the start of narcosis (100 mg/kg of thiobutabarbital, administered intraperitoneally).

The arrhythmogenous substance used was aconitine, administered by intravenous infusion (at the rate of 0.005 mg/kg. minute) 60 minutes after administration of the benzisothiazole derivative. In untreated animals (N=30) arrhythmias manifest themselves after an average of 3.7±0.9 minutes; their occurence can be delayed by antiarrhythmic agents, the delay being dependent on the dosage.

for a quantitative evaluation of the linear relation between the logarithm of the dose (mg/kg) of the test substances and the relative increase in the duration of infusion of aconitine (Δ%), the dose which increases the duration of infusion by 50% (ED 50%) was determined. The conventional antiarrhythmic agent procainamide was used for comparison.

The acute toxicity was determined on groups of 10 or 20 female Swiss mice weighing 20–26 g, using intraperitoneal administration. The LD 50 was calculated (Probit analysis) as the dose following which 50% of the animals died within 7 days.

Table 1 shows that the antiarrhythmic activity of the compounds of Examples 2 and 3 is about 5 times greater than that of the antiarrhythmic agent procainamide. A further advantage of the novel compounds is that the effect at the maximum dose is 114% (Example 2) or 73% (Example 3) higher than that of procainamide, i.e. the aconitine-antagonism of the tested compounds is substantially more pronounced than that of procainamide.

The therapeutic range, expressed as the quotient of the lethal dose (LD 50) and the antiarrhythmically active dose (ED 50% is 4 times greater (Example 2) or 2.8 times greater (Example 3) than for procainamide.

priate dose with the conventional excipients or diluents and the conventional pharmaceutical auxiliaries, in accordance with the desired route of administration.

The preferred formulations are those suitable for oral administration. Examples of these are tablets, film tablets, dragees, capsules, pills, powders, solutions and suspensions, and forms which exert a depot effect.

Of course, formulations for parenteral administration, eg. injection solutions or additives for infusion solutions, may also be used. Suppositories are a further example of suitable formulations.

Appropriate tablets can be obtained, for example, by mixing the active ingredient with conventional auxiliaries, for example inert diluents, eg. dextrose, sugar, sorbitol, mannitol, polyvinylpyrrolidone, calcium carbonate, calcium phosphate or lactose, disintegrating agents, eg. corn starch, alginic acid or polyvinylpyrrolidone, binders, eg. starch or gelatin, lubricants, eg. magnesium stearate or talc and/or agents added in order to achieve a depot effect, eg. carboxypolymethylene, carboxymethylcellulose, cellulose acetate phthalate or polyvinyl acetate. The tablets may also consist of several layers.

Similarly, dragees can be prepared by coating cores, prepared similarly to the above tablets, with conventional dragee-coating agents, eg. collidone or shellac, gum arabic, talc, titanium dioxide or sugar. The dragee coating may also consist of several layers, and the auxiliaries mentioned above, in connection with tablets, may be used.

Solutions or suspensions containing the active ingredients according to the invention may in addition contain flavor improvers, eg. saccharin, cyclamate or sugar, as well as flavorings, e.g. vanillin or orange extract. In addition, they may contain suspension assistants, eg. sodium carboxymethylcellulose, or preservatives, eg. parahydroxybenzoates. Capsules containing active ingredients may be prepared, for example, by mixing the active ingredient with an inert carrier, eg. lactose or sorbitol, and encapsulating the mixture in gelatin capsules.

Suitable suppositories may be prepared, for example, by mixing (the active ingredient) with an appropriate excipient, eg. a neutral fat or a polyethylene glycol or a derivative thereof.

For use in man, a single dose of the compound according to the invention is from 5 to 100 mg, preferably from 10 to 80 mg.

In the Examples which follow, parts are by weight and bear the same relation to parts by volume as that of the kilogram to the liter.

TABLE 1

| | Antiarrhythmic effect and acute toxicity | | | | | | |
|---|---|---|---|---|---|---|---|
| | Antiarrhythmic effect[1] | | | | | Acute toxicity | |
| | Effective dose | | Maximum effect[4] | | | LD 50 | Therapeutic |
| Compound | ED 20%[2] | R.E.[3] | Dose | Δ%[5] | R.M.E.[6] | mg/kg | range[7] |
| Example 2 | 31.2 | 5.03 | 215 | 289 | 2.14 | 126 | 4.03 |
| Example 3 | 32.7 | 4.80 | 215 | 233 | 1.73 | 90.5 | 2.76 |
| Procainamide | 157 | 1.00 | 681 | 135 | 1.00 | 227 | 1.00 |

[1] Aconitine-induced arrhythmia in rats
[2] Orally administered dose (mg/kg) which increases the duration of aconitine infusion (min) by 50%
[3] R.E. = relative effect; procainamide = 1.00
[4] Effect of the maximum non-toxic dose
[5] Increase in duration of aconitine infusion, Δ%
[6] R.M.E. = relative maximum effectiveness
[7] $\frac{LD\ 50}{ED\ 50\%}$ The therapeutic agents or formulations are prepared in the conventional manner by compounding an appro-

EXAMPLE 1

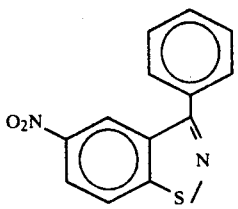

26.15 parts of 2-chloro-5-nitrobenzophenone and 3.2 parts of sulfur in 300 parts of methanol are reacted with 40 parts of $NH_3$ under a pressure of 5 bars at 80° C. for 6 hours in a tantalum autoclave. The reaction mixture is cooled to 25° C., the pressure is released and the solid which has precipitated is filtered off. The resulting crystals are washed chloride-free with water and are dried. 24 parts of 3-phenyl-5-nitro-1,2-benzisothiazole, melting at 130° C., are obtained. The yield corresponds to 94% of theory.

EXAMPLE 2

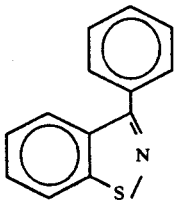

216.5 parts of 2-chlorobenzophenone, 32 parts of sulfur and 100 parts of $NH_3$ in 1,000 parts of glycol monomethyl ether are reacted for 6 hours at 160° C. in a tantalum autoclave. After cooling, and releasing the pressure, the reaction mixture is substantially freed from the solvent, 500 parts of water are added to the residue and the mixture is extracted with 3×200 parts of methylene chloride. The combined methylene chloride solution is worked up by distillation. 164 parts of 3-phenyl-1,2-benzisothiazole are obtained at 150°–155° C./1 mm Hg; the material melts at 70° C. The yield corresponds to 78% of theory.

EXAMPLE 3

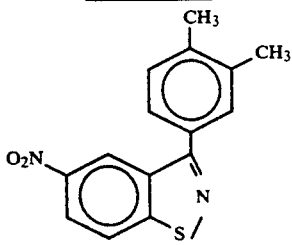

145 parts of 2-chloro-5-nitro-3',4'-dimethylbenzophenone, 16 parts of sulfur and 100 parts of $NH_3$ in 800 parts of methanol are reacted for 10 hours at 80° C. in a tantalum autoclave. The contents of the autoclave are then filtered and the filter residue is washed with water. 134 parts of 3-(3',4'-dimethylphenyl)-5-nitro-1,2-benzisothiazole, melting at 154° C., are obtained. The yield corresponds to 94% of theory.

EXAMPLE 4

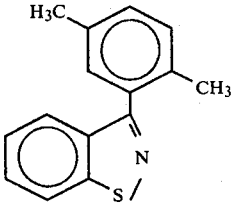

245.5 parts of 2-chloro-2',5'-dimethylbenzophenone, 32 parts of sulfur and 100 parts of ammonia in 800 parts of methylglycol are reacted for 6 hours at 160° C. in an enamelled autoclave. After cooling the mixture and releasing the pressure, the solvent is substantially distilled off and the residue is washed with water and recrystallized from 1,000 parts of methanol. 192 parts of 3-(2',5'-dimethylphenyl)-1,2-benzisothiazole, of melting point 87° C., are obtained. The yield corresponds to 80% of theory.

EXAMPLE 5

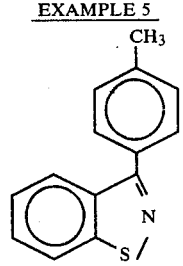

230.5 parts of 2-chloro-4'-methylbenzophenone, 32 parts of sulfur and 100 parts of $NH_3$ in 800 parts of methylglycol are reacted for 6 hours at 160° C. in an enamelled autoclave. 200 parts of 3-(4'-methylphenyl)-1,2-benzisothiazole, of melting point 56° C., are obtained. The yield corresponds to 89% of theory.

In a similar manner, and using the same conditions and molar ratios, 2,5-dichloro-4'-methylbenzophenone is used to prepare 5-chloro-3-(4'-methylphenyl)-,2-benzisothiazole, of melting point 121° C. (yield, 85% of theory), and 2-chloro-5-nitro-4'-methylbenzophenone is used to prepare 5-nitro-3-(4'-methylphenyl)-1,2-benzisothiazole, of melting point 179° C. (yield, 90% of theory).

EXAMPLE 6

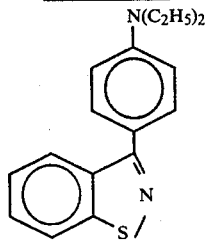

28.75 parts of 2-chloro-4'-diethylaminobenzophenone, 3.2 parts of sulfur and 50 parts of $NH_3$ in 400 parts of glycol monoethyl ether are reacted for 20 hours at 160° C. in a tantalum autoclave. The material discharged from the autoclave is concentrated completely, the residue is taken up in 500 parts of water and the mixture is extracted with 3×200 parts of methylene chloride. The organic phase is dried and concentrated. After recrystallization from methanol, 20 parts of 3-(4'-diethylaminophenyl)-1,2-benzisothiazole, melting at 85° C., are obtained. The yield corresponds to 71% of theory.

EXAMPLE 7

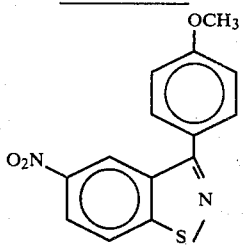

291.5 parts of 2-chloro-5-nitro-4'-methoxybenzophenone, 32 parts of sulfur and 100 parts of ammonia in 1,000 parts of methanol are reacted for 5 hours at 80° C. in an enamelled autoclave. The contents of the autoclave are filtered and the residue is washed with water and dried. 280 parts of 3-(4'-methoxyphenyl)-5-nitro-1,2-benzisothiazole, melting at 207° C., are obtained. The yield corresponds to 97% of theory. corresponds to 97% of theory.

EXAMPLE 8

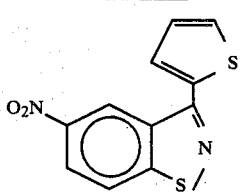

26.7 parts of 2-(2'-chloro-5'-nitrobenzoyl)-thiophene, 3.2 parts of sulfur and 50 parts of $NH_3$ in 200 parts of methanol are reacted for 10 hours at 80° C. in a tantalum autoclave. The contents of the autoclave are filtered and the filter residue is washed with water and recrystallized from methylglycol. 21 parts of 5-nitro-3-(thien-2'-yl)-1,2-benzisothiazole, melting at 164° C., are obtained. The yield corresponds to 80% of theory.

EXAMPLE 9

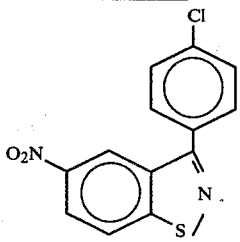

29.6 parts of 2-chloro-5-nitro-4'-chlorobenzophenone, 3.2 parts of sulfur and 50 parts of $NH_3$ in 500 parts of methanol are reacted for 24 hours at 80° C. in a tantalum autoclave. The contents of the autoclave are filtered and the filter residue is washed with water and dried. 26 parts of 3-(4'-chlorophenyl)-5-nitro-1,2-benzisothiazole, melting at 226° C., are obtained. The yield corresponds to 89% of theory.

The Use Examples which follow further illustrate the present invention.

A. Example of the preparation of a compound of the formula Ib from a 1,2-benzisothiazole I by chlorination.

3-(4-Chloromethylphenyl)-1,2-benzisothiazole 225 parts of 3-(4-methylphenyl)-1,2-benzisothiazole are heated to 170° C. in a stirred apparatus and 100 parts of chlorine are passed in over 2 hours whilst irradiating the mixture with a UV lamp. The end point of the reaction is determined by gas chromatography (disappearance of the starting material). The reaction mixture is then cooled and the product is filtered off and recrystallized from methanol. 208 parts of 3-(4-chloromethylphenyl)-1,2-benzisothiazole, melting at 86°-89° C., are obtained; this yield corresponds to 80% of theory.

5-Chloro-3-(4'-chloromethylphenyl)-1,2-benzisothiazole, melting at 116° C., is prepared similarly, under the same conditions and with the same molar ratios.

B. Preparation of the compounds IV.

USE EXAMPLE 1

3-[4'-(Imidazolin-2"-yl)-phenyl]-1,2-benzisothiazole

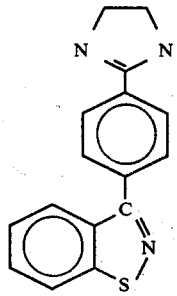

26 parts of 3-(4'-chloromethylphenyl)-1,2-benzisothiazole, 6.4 parts of sulfur and 300 parts of toluene are heated to 50° C. and 12 parts of ethylenediamine are added slowly at this temperature. The reaction mixture is then stirred for 15 hours under reflux and is filtered hot, and the filtrate is cooled to 10°-15° C. 21 parts of 3-(4'-imidazolin-2"-yl-phenyl)-1,2-benzisothiazole, melting at 177° C., are obtained. This corresponds to a yield of 75% of theory. The hydrochloride of the compound melts at 318° C.

USE EXAMPLE 2

3-[4'-(Tetrahydropyrimidin-2"-yl)-phenyl]-1,2-benzisothiazole hydrochloride

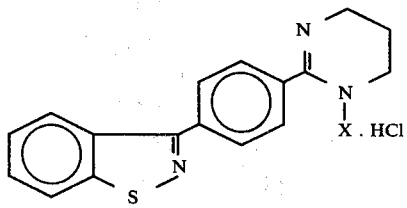

26 parts of 3-(4'-chloromethylphenyl)-1,2-benzisothiazole, 6.4 parts of sulfur and 300 parts of toluene are heated to 50° C. 15 parts of 1,3-diaminopropane are added slowly at the same temperature. The reaction mixture is then stirred for 20 hours under reflux. 20 parts of hydrogen chloride gas are then passed in over one hour, the mixture is cooled to room temperature and the resulting solid is filtered off. After recrystallization from water in the presence of active charcoal, 18 parts of 3-[4'-tetrahydropyrimidin-2''-yl)-phenyl]-1,2-benzisothiazole hydrochloride, melting, with decomposition, at 314° C., are obtained. The yield corresponds to 54.6% of theory.

USE EXAMPLE 3

3-[4'-(Methylimidazolin-2''-yl)-phenyl]-1,2-benzisothiazole hydrochloride

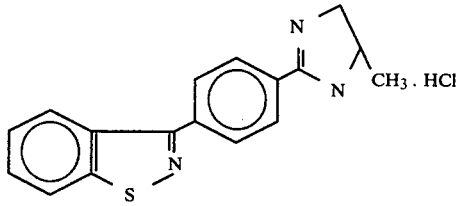

26 parts of 3-(4'-chloromethylphenyl)-1,2-benzisothiazole, 6.4 parts of sulfur and 15 parts of 1,2-diaminopropane in 400 parts of glycol monomethyl ether are heated for 15 hours at 110° C. After distilling off the solvent, the residue is dissolved in 50 parts of methanol and this solution is stirred into 400 parts of ethereal hydrochloric acid (15 parts of HCl in diethyl ether), whist cooling. The crystals fromed are filtered off and dissolved in 300 parts of water, the solution is filtered and the filtrate is rendered alkaline with concentrated NaOH and extracted with methylene chloride. The methylene chloride phase is dried and 20 parts of hydrogen chloride gas are passed in. 17 parts of the desired end product are obtained as colorless crystals, melting at 243° C. The yield corresponds to 52% of theory.

USE EXAMPLE 4

5-Chloro-3-[4'-(imidazolin-2''-yl)-phenyl]-1,2-benzisothiazole

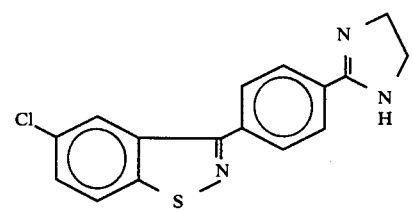

44 parts of 5-chloro-3-(4'-chloromethylphenyl)-1,2-benzisothiazole, 9.6 parts of sulfur and 18 parts of ethylenediamine in 500 parts of toluene are refluxed for 20 hours. The reaction mixture is filtered hot, the filtrate is cooled and the resulting crystals are filtered off. After recrystallization from toluene in the presence of active charcoal, 26 parts of 5-chloro-3-[4'-(imidazolin-2''-yl)-phenyl]-1,2-benzisothiazole, melting at 195° C., are obtained. The yield corresponds to 55% of theory.

USE EXAMPLE 5

5-Chloro-3-[4'-(methylimidazolin-2''-yl)-phenyl]-1,2-benzisothiazole hydrochloride

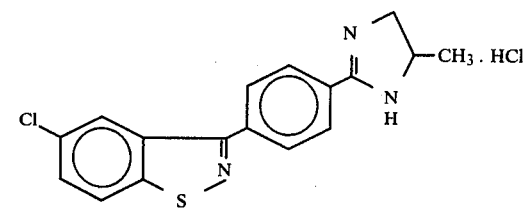

44 parts of 5-chloro-3-(4'-chloromethylphenyl)-1,2-benzisothiazole, 9.6 parts of sulfur and 22.5 parts of 1,2-diaminopropane in 600 parts of toluene are refluxed for 24 hours. The reaction mixture is filtered hot and the filtrate is concentrated on a rotary evaporator. The residue is dissolved in 500 parts of ether and 30 parts of hydrogen chloride gas are passed into the solution, whilst cooling. The resulting crystals are filtered off and recrystallized from water. 31 parts of 5-chloro-3-[4'-(methylimidazolin-2''-yl)-phenyl]-1,2-benzisothiazole hydrochloride, melting, with decomposition, at 248° C., are obtained. The yield corresponds to 57% of theory.

USE EXAMPLES 6–9

Formulation Examples prepared in the conventional manner:

| 6. Tablets: | | |
|---|---|---|
| (a) | An active ingredient of the formula IV | 5 mg |
| | Lactose | 200 mg |
| | Methylcellulose | 15 mg |
| | Corn starch | 50 mg |
| | Talc | 11 mg |
| | Magnesium stearate | 4 mg |
| | | 285 mg |
| (b) | An active ingredient of the formula IV | 20 mg |
| | Lactose | 178 mg |
| | Avicel | 80 mg |
| | Polywax 6000 | 20 mg |
| | Magnesium stearate | 2 mg |
| | | 300 mg |
| (c) | An active ingredient of the formula IV | 50 mg |
| | Polyvinylpyrrolidone (mean molecular weight 25,000) | 170 mg |
| | Polyethylene glycol (mean molecular weight 4,000) | 14 mg |
| | Hydroxypropylmethylcellulose | 40 mg |
| | Talc | 4 mg |
| | Magnesium stearate | 2 mg |
| | | 280 mg |

The active ingredient is moistened with a 10 percent strength aqueous solution of polyvinylpyrrolidone, forced through a sieve of 1.0 mm mesh width and dried at 50° C. The resulting granules are mixed with the polyethylene glycol (mean molecular weight 4,000), hydroxypropylmethylcellulose, talc and magnesium stearate and the mixture is pressed to give tablets weighing 280 mg each.

| 7. Example of drages: | |
|---|---|
| An active ingredient of the formula IV | 60 mg |
| Lactose | 90 mg |
| Corn starch | 60 mg |
| Polyvinylpyrrolidone | 6 mg |

| -continued | |
|---|---|
| 7. Example of drages: | |
| Magnesium stearate | 1 mg |
| | 217 mg |

The mixture of the active ingredient with lactose and corn starch is moistened with an 8% strength aqueous solution of polyvinylpyrrolidone, granulated by passing through a 1.5 mm sieve, dried at 50° C. and then forced through a 1.0 mm sieve. The resulting granules are mixed with magnesium stearate and pressed to form dragee cores. The resulting cores are coated in the conventional manner with a covering consisting essentially of sugar and talc.

| 8. Capsule formulation: | |
|---|---|
| An active ingredient of the formula IV | 5.0 mg |
| Magnesium stearate | 2.0 mg |
| Lactose | 19.3 mg |

| 9. Injection solution: | |
|---|---|
| An active ingredient of the formula IV | 10 mg |
| Sodium chloride | 9 mg |
| Distilled water, to make up to 1.0 ml. | |

We claim:

1. A method of treating cardiac arrhythmia in humans and animals, comprising the administration of an effective amount of a 1,2-benzisothiazole of the formula

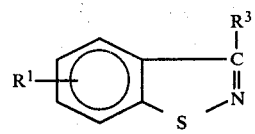

where $R^1$ is hydrogen; alkyl of 1 to 6 carbon atoms; alkyl of 1 to 6 carbon atoms substituted by carboxamido; cycloalkyl of 5 to 12 carbon atoms; phenyl or naphthyl, either of which may be fused; fused naphthoquinon-1,4-ylene; halogen; alkoxy of 1 to 4 carbon atoms, nitro, or

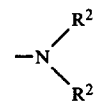

where:
the radicals $R^2$ are identical or different and each is hydrogen, alkyl of 1 to 6 carbon atoms, alkenyl of 3 to 6 carbon atoms, cycloalkyl of 5 to 8 carbon atoms, aralkyl of 7 to 12 carbon atoms or phenyl; $R^3$ is chloromethylphenyl, phenyl or naphthyl; phenyl or naphthyl which is substituted by one or two alkyl of 1 to 4 carbon atoms, alkoxy of 1 to 4 carbon atoms, chlorine, bromine or dialkylamino of 1 to 4 carbon atoms in the alkyl; or $R^3$ is a 5-membered or 6-membered heterocyclic ring which contains either two nitrogen atoms, or one nitrogen atom, or one oxygen atom, or one sulfur atom, or one nitrogen atom along with one sulfur atom, or one nitrogen atom along with one oxygen atom, or one oxygen atom with one sulfur atom.

* * * * *